(12) United States Patent
Gwak et al.

(10) Patent No.: US 9,963,421 B2
(45) Date of Patent: May 8, 2018

(54) REFINING METHOD OF ORGANIC AMINE

(71) Applicant: CJ CHEILJEDANG CORP., Seoul (KR)

(72) Inventors: Won Sik Gwak, Yongin-si (KR); Hyun Ju Won, Seoul (KR); Hideki Murata, Seoul (KR); Chong Ho Lee, Seoul (KR)

(73) Assignee: CJ CHEILJEDANG CORP., Seoul (KR)

( * ) Notice: Subject to any disclaimer, the term of this patent is extended or adjusted under 35 U.S.C. 154(b) by 0 days. days.

(21) Appl. No.: 14/767,814

(22) PCT Filed: Mar. 19, 2015

(86) PCT No.: PCT/KR2015/002657
§ 371 (c)(1),
(2) Date: Aug. 13, 2015

(87) PCT Pub. No.: WO2015/152541
PCT Pub. Date: Oct. 8, 2015

(65) Prior Publication Data
US 2017/0015616 A1    Jan. 19, 2017

(30) Foreign Application Priority Data
Apr. 4, 2014    (KR) .................. 10-2014-0040743

(51) Int. Cl.
*C07C 209/84*    (2006.01)
*C07C 211/09*    (2006.01)
*C12P 13/00*    (2006.01)

(52) U.S. Cl.
CPC .......... *C07C 209/84* (2013.01); *C07C 211/09* (2013.01); *C12P 13/001* (2013.01)

(58) Field of Classification Search
CPC ..... C07C 209/84; C07C 211/09; C12P 13/001
See application file for complete search history.

(56) References Cited

U.S. PATENT DOCUMENTS 5,731,440 A    3/1998   Yoshizawa et al.
8,334,411 B2 *  12/2012  Ito ........................ B01D 61/027
                                                         564/138

(Continued)

FOREIGN PATENT DOCUMENTS

EP    2263996 A1    12/2010
JP    07291934 A    11/1995

(Continued)

OTHER PUBLICATIONS

International Search Report with English Translation for International Application No. PCT/KR2015/002657 dated Jun. 24, 2015.

(Continued)

*Primary Examiner* — Sudhakar Katakam
*Assistant Examiner* — Jennifer C Sawyer
(74) *Attorney, Agent, or Firm* — Cantor Colburn LLP

(57) ABSTRACT

Provided are a method of refining a reaction solution including a carbonate of 1,5-diaminopentane, which is produced by fermentation, through a decarbonation step and a pH adjustment step, and 1,5-diaminopentane which is refined by the above method.

9 Claims, 1 Drawing Sheet

(56) References Cited

U.S. PATENT DOCUMENTS

| | | | |
|---|---|---|---|
| 8,906,653 B2 * | 12/2014 | Volkert | C07C 209/84 |
| | | | 210/601 |
| 2006/0217549 A1 | 9/2006 | Letourneur et al. | |
| 2010/0292429 A1 | 11/2010 | Volkert et al. | |
| 2011/0004018 A1 | 1/2011 | Ito et al. | |

FOREIGN PATENT DOCUMENTS

| | | | |
|---|---|---|---|
| JP | 2004000114 A | 1/2004 | |
| JP | 2009155284 A | 7/2009 | |
| KR | 1020100117084 A | 11/2010 | |
| KR | 1020100133366 A | 12/2010 | |
| RU | 2330837 C2 | 6/2004 | |
| WO | 2006123778 A1 | 11/2006 | |

OTHER PUBLICATIONS

Written Opinion with English Translation for International Application No. PCT/KR2015/002657 dated Jun. 24, 2015.
Chinese Office Action for Application No. 201580000357.2 dated Jul. 27, 2016.
Extended European Search Report for Application No. 15750229.5 dated Nov. 24, 2016, citing the above reference(s).
Russian Office Action for Application No. 2015136585 dated Nov. 3, 2016, citing the above reference(s).

* cited by examiner

REFINING METHOD OF ORGANIC AMINE

TECHNICAL FIELD

The inventive concept relates to a refining method of 1,5-diaminopentane.

BACKGROUND ART 1,5-diaminopentane (cadaverine) may be prepared by removing microorganisms from a lysine fermentation broth and then removing a carboxyl group therefrom using lysine decarboxylase (LDC). Alternatively, 1,5-diaminopentane may be directly prepared by using a microorganism having decarboxylase activity. The 1,5-diaminopentane may be obtained in the form of a salt, such as sulfate and carbonate, according to preparation methods.

For example, 1,5-pentanediamine adipate may be recovered as a crystal by adding adipic acid to a sulfate of 1,5-diaminopentane. Alternatively, a carbonate of 1,5-diaminopentane may be directly recovered as a crystal.

However, since the above preparation methods have low yields and 1,5-diaminopentane is obtained in the form of a salt, an additional process is required to remove the salt and obtain pure 1,5-diaminopentane.

Thus, there is a need to develop a method of effectively and directly refining 1,5-diaminopentane from the fermentation broth.

DETAILED DESCRIPTION OF THE INVENTIVE CONCEPT

Technical Problem

The inventive concept provides a novel method of refining 1,5-diaminopentane.

The inventive concept also provides 1,5-diaminopentane which is refined by the above method.

Technical Solution

According to an aspect of the inventive concept, there is provided a method of refining 1,5-diaminopentane including: concentrating a fermentation broth including a carbonate of 1,5-diaminopentane; adding an acid to a concentrate of the fermentation broth to prepare a carbonate removed acidic composition with a pH of about 4 to about 7.0; adding a base to the acidic composition to prepare a basic composition with a pH of about 12.0 to about 14; and recovering 1,5-diaminopentane from the basic composition.

According to another aspect of the inventive concept, there is provided 1,5-diaminopentane which is refined by the above method.

Advantageous Effects

According to an aspect of the inventive concept, high-purity 1,5-diaminopentane may be obtained with a high yield by adding an acid to a fermentation broth including a carbonate of 1,5-diaminopentane to remove carbonate and then adding a base thereto.

BEST MODE

Figure 1:
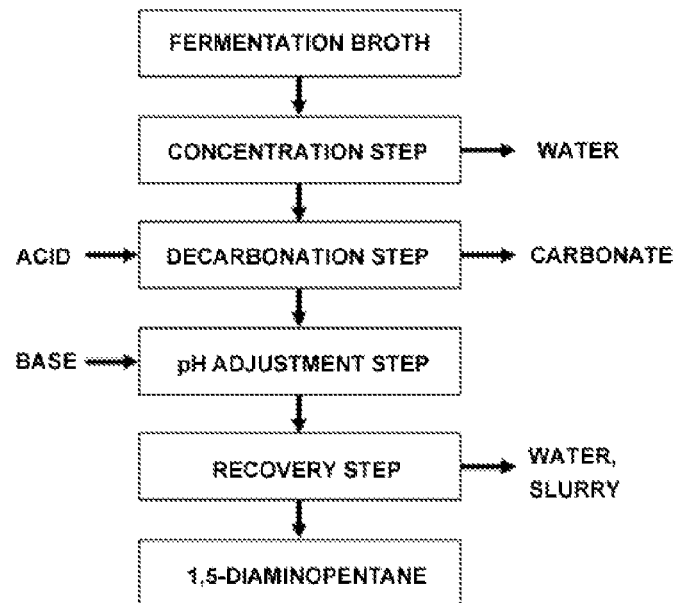
FIG. 1 is a flowchart of a method of refining 1,5-diaminopentane according to Example 1.

Hereinafter, a method of refining 1,5-diaminopentane according to an exemplary embodiment of the inventive concept and 1,5-diaminopentane refined by the above method will be described in more detail.

The method of refining 1,5-diaminopentane according to the embodiment of the inventive concept may include the steps of: concentrating a fermentation broth including a carbonate of 1,5-diaminopentane; adding an acid to a concentrate of the fermentation broth to prepare a carbonate removed acidic composition with a pH of about 4 to about 7.0; adding a base to the acidic composition to prepare a basic composition with a pH of about 12.0 to about 14; and recovering 1,5-diaminopentane from the basic composition.

The refining method may simply obtain high-purity 1,5-diaminopentane with a high yield in such a manner that a neutral fermentation broth including a carbonate of 1,5-diaminopentane is concentrated to prepare a concentrate of the fermentation broth, an acid is then added to the concentrate to prepare an acidic composition from which carbonate is removed, a base is added to the acidic composition to separate 1,5-diaminopentane from a non-carbonate of 1,5-diaminopentane, and 1,5-diaminopentane is then selectively recovered.

For example, 1,5-diaminopentane is generated by using lysine decarboxylase in a lysine fermentation broth or by fermenting microorganisms including lysine decarboxylase, and simultaneously, a carbonate, a by-product of decarboxylation of lysine, is reacted with the generated 1,5-diaminopentane to form a carbonate of 1,5-diaminopentane. Thus, a fermentation broth including a carbonate of 1,5-diaminopentane may be prepared.

In the concentrating of the fermentation broth, a portion of a solvent included in the fermentation broth may be removed and this corresponds to a primary concentration step. A concentration of the 1,5-diaminopentane included in the fermentation broth may be increased by removing the portion of the solvent. The solvent, for example, is water. For example, in the concentrating of the neutral fermentation broth, about 40% or more, preferably about 50% or more, more preferably about 60% or more, and most preferably about 70% or more of the initial solvent included in the unconcentrated fermentation broth may be removed.

The concentrating of the fermentation broth in the refining method may be performed at a vapor temperature of about 100° C. or less. That is, the concentration may be performed under a condition in which the temperature of a vapor evaporated from the fermentation broth is about 100° C. or less. For example, the concentrating of the fermentation broth in the refining method may be performed in a vapor temperature range of about 10° C. to about 100° C., preferably about 30° C. to about 80° C., and more preferably about 45° C. to about 70° C. The solvent may be more easily removed under the above condition.

The concentrating of the fermentation broth in the refining method may be performed at a reduced pressure of about 760 mmHg or less. That is, the concentration may be performed under a condition in which the pressure of a vapor in equilibrium with the fermentation broth is about 760 mmHg or less. For example, the concentrating of the fermentation broth in the refining method may be performed at a pressure of about 10 mmHg to about 760 mmHg, preferably about 40 mmHg to about 500 mmHg, and more preferably about 70 mmHg to about 200 mmHg. The solvent may be more easily removed under the above condition.

An amount of the solvent included in the concentrate (i.e., concentration product), which is obtained by concentrating the fermentation broth, may be in a range of about 10 wt % to about 50 wt % based on a total weight of the concentrate. For example, the amount of the solvent of the concentrate may be in a range of about 15 wt % to about 45 wt %, preferably about 20 wt % to about 42 wt %, based on the total weight of the concentration product. The solvent may be water.

A pH of the fermentation broth is neutral and is preferably in a range of about 7.0 to about 8.0, and a pH of the concentrate obtained by concentrating the fermentation broth is in a range of about 8.0 to about 9.0.

The concentrate includes a carbonate of 1,5-diaminopentane, and a reaction, which generates a non-carbonate of 1,5-diaminopentane by removing carbonate from the carbonate of the 1,5-diaminopentane, may be represented by the following Reaction Formula 1. The expression "acidic composition" in the refining method denotes a composition in which 1,5-diaminopentane is included in the form of a non-carbonate by removing a carbonate from the fermentation broth.

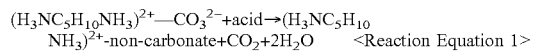
$(H_3NC_5H_{10}NH_3)^{2+}-CO_3^{2-}+acid \rightarrow (H_3NC_5H_{10}NH_3)^{2+}$-non-carbonate$+CO_2+2H_2O$  <Reaction Equation 1>

As illustrated in Reaction Equation 1, carbonate ions in a carbonate of diaminopentane react with an acid to be decomposed into water and carbon dioxide, and the carbon dioxide is removed by evaporation.

In the refining method, the acid usable in a decarboxylation process may be at least one selected from the group consisting of hydrochloric acid, sulfuric acid, phosphoric acid, acetic acid, and nitric acid. However, the inventive concept is not necessarily limited thereto, and any acid may be used as long as it may adjust the pH of the composition to be acidic and is used in the art. The acid used in the decarboxylation process may be a gas phase, a liquid phase, or a mixed phase thereof.

In the refining method, a pH of the acidic composition may be less than about 7.0 and may be preferably in a range of about 4.0 to about 5.0. In a case where the pH of the acidic composition is about 7.0 or more, since a carbonate is not separated from the carbonate of the 1,5-diaminopentane in some of the carbonate of the 1,5-diaminopentane, the 1,5-diaminopentane is not converted into a free form in the preparing of the basic composition. Thus, the separation of the 1,5-diaminopentane in a distillation step may be difficult. As a result, a recovery rate of the 1,5-diaminopentane may be reduced.

When the amount of the solvent in the carbonate removed acidic composition, is excessively small, a large amount of salt may be precipitated in the preparing of the basic composition. In contrast, when the amount of the solvent in the carbonate removed acidic composition is excessively large, it may take a long time to remove the 1,5-diaminopentane from the basic composition. The solvent may be water. For example, the amount of the solvent in the acidic composition may be in a range of about 35 wt % to about 45 wt % based on a total weight of the acidic composition.

In the refining method, the base used in the preparation of the basic composition may be at least one selected from the group consisting of sodium hydroxide, calcium hydroxide, magnesium hydroxide, potassium hydroxide, barium hydroxide, and ammonium hydroxide. However, the inventive concept is not necessarily limited thereto, and any base may be used as long as it may adjust the pH of the composition to be basic and is used in the art.

In the refining method, a pH of the basic composition may be about 12 or more and may be preferably in a range of about 12.0 to about 14.0. In a case where the pH of the basic composition is less than about 12.0, since a portion of the 1,5-diaminopentane may be present in a state of being combined with the non-carbonate, the separation of the 1,5-diaminopentane by distillation may be difficult. As a result, the recovery rate of the 1,5-diaminopentane may be reduced.

In the refining method, the recovering of the 1,5-diaminopentane may be performed before the carbonate of the 1,5-diaminopentane is regenerated in the basic composition. As the time elapsed, since a carbonate of 1,5-diaminopentane may be formed by combining 1,5-diaminopentane in the basic composition and carbon dioxide in the air, the amount of the 1,5-diaminopentane, which may be recovered by the distillation, may be reduced. Thus, 1,5-diaminopentane may be recovered immediately after or simultaneously with the preparation of the basic composition.

Specifically, the recovering of the 1,5-diaminopentane from the basic composition in the refining method may include a secondary concentration step for separating a composition including 1,5-diaminopentane from the basic composition by distillation and a step of fractional distillating the 1,5-diaminopentane from the composition including 1,5-diaminopentane.

For example, the composition including 1,5-diaminopentane is separated from the basic composition and stored, and the separated composition may then be used in the recovering of the 1,5-diaminopentane if necessary. The composition including 1,5-diaminopentane denotes a composition in which the amount of the 1,5-diaminopentane among its components is greater than that of the basic composition, but is smaller than that of a final refined product.

In the refining method, the composition including 1,5-diaminopentane may be a gas phase, a liquid phase, or a mixed phase thereof. That is, a state of the composition including 1,5-diaminopentane may be changed according to conditions required for the refining method.

In the separating of the composition including 1,5-diaminopentane, a vapor and/or a condensate including 1,5-diaminopentane are recovered by distillation. The separating may be performed in a double-jacketed reactor.

In the refining method, the separating of the composition including 1,5-diaminopentane may be performed in a vapor temperature range of about 30° C. to about 180° C. and in a pressure range of about 10 mmHg to about 760 mmHg, and may be preferably performed in a vapor temperature range of about 40° C. to about 120° C. and in a pressure range of about 60 mmHg to about 200 mmHg. The composition including 1,5-diaminopentane may be separated with a high yield under the above condition. The composition including 1,5-diaminopentane, which is separated within the above temperature and pressure ranges, may be obtained in a liquid phase by condensation.

The storage of the composition including 1,5-diaminopentane, for example, may be performed by a reservoir which is disposed between the top of the reactor and a distillation column. However, the inventive concept is not necessarily limited to the above-described configuration, and any storage method may be used as long as it is used in the art.

Alternatively, in the refining method, the separating of the composition including 1,5-diaminopentane by the distillation and the recovering of the 1,5-diaminopentane by the fractional distillation may be continuously performed. That is, the composition including 1,5-diaminopentane is separated from the basic composition by the distillation and is simultaneously again separated into 1,5-diaminopentane and other components by the fractional distillation so that 1,5-diaminopentane may be recovered. The 1,5-diaminopentane obtained by the fractional distillation is a final product.

In the refining method, the recovering of the 1,5-diaminopentane may be performed in the distillation column. For example, 1,5-diaminopentane may be selectively recovered by continuously introducing the composition including 1,5-diaminopentane as a main component, which is evaporated in the reactor including the basic composition, into the distillation column. For example, the composition including 1,5-diaminopentane may be introduced into an intermediate position of the distillation column, but an input position may vary according to specific reaction conditions and conditions of the distillation column.

In the refining method, the distillation column may be operated in a vapor temperature range of about 30° C. to about 180° C. and in a pressure range of about 10 mmHg to about 760 mmHg. For example, the distillation column may be operated in a vapor temperature range of about 40° C. to about 120° C. and in a pressure range of about 60 mmHg to about 200 mmHg. 1,5-diaminopentane may be obtained with a high yield within the above temperature and pressure ranges.

In the refining method, 1,5-diaminopentane may be recovered from a bottom of the distillation column, and water and ammonia, for example, may be recovered from a top of the distillation column.

In the refining method, the composition including 1,5-diaminopentane as a main component is removed and a by-product may then be recovered from the remaining basic composition. For example, the composition including 1,5-diaminopentane as a main component is removed from the basic composition and a by-product may then be recovered from a remaining slurry through additional refining. Also, in a case where the slurry includes a microorganism, the slurry is completely dissolved by further adding distilled water to the slurry to separate the microorganism, and a by-product may then be recovered.

For example, 1,5-diaminopentane may be refined as follows.

Fermentation Step

First, a fermentation broth including L-Lysine and its salt is prepared by culturing a microorganism, and, after removing the microorganism from the fermentation broth, a fermentation broth including 1,5-diaminopentane may be prepared by enzyme conversion reaction. About 58% of the 1,5-diaminopentane included in the prepared fermentation broth is in the form of carbonate and about 42% thereof is in the form of sulfate.

Primary Concentration Step (Water Removal Step)

Next, water is removed from the fermentation broth to concentrate the fermentation broth.

A method used in the removal of the water may include a vacuum concentration method and/or an evaporative concentration method. A type of concentrator used in the method is not particularly limited, and any concentrator selected from the group consisting of a centrifugal concentrator, an evaporation concentrator, a natural circulating concentrator, a low temperature vacuum concentrator, a rotary vacuum concentrator, a vacuum evaporation concentrator, a thin film concentrator, and a planar concentrator may be used.

For example, the concentration may be performed using a low temperature vacuum concentration method among the above-described concentration methods. Specifically, the concentration of the fermentation broth, from which the microorganism is removed or not removed, may be performed in a vapor temperature range of about 10° C. to about 100° C., for example, about 45° C. to about 70° C., and in a pressure range of about 10 mmHg to about 760 mmHg, for example, about 70 mmHg to about 200 mmHg. An amount of the water in the concentrate, from which the water is removed, may be in a range of about 15 wt % to about 45 wt %, for example, about 20 wt % to about 43 wt %, and, for example, about 30 wt % to about 42 wt % based on a total weight of the concentrated fermentation broth.

Decarbonation Step (Preparation Step of Acidic Composition from which Carbonate is Removed)

Next, an acidic composition is prepared by adding an acid to the concentrated fermentation broth.

Carbonate is removed by decreasing a pH of the concentrated fermentation broth by making the concentrated fermentation broth to be acidic. The acid used in the decarbonation step may be at least one selected from the group consisting of hydrochloric acid, sulfuric acid, phosphoric acid, acetic acid, and nitric acid. However, the inventive concept is not necessarily limited thereto, and any acid may be used as long as it may adjust a pH of the composition to be acidic, i.e., less than about 7.0, and is used in the art.

For the decarbonation in the refining method, the pH of the composition may be less than about 7.0 and, for example, may be in a range of about 4.0 to about 5.0. In a case where the pH of the acidic composition is about 7.0 or more, since a carbonate is not separated from the carbonate of the 1,5-diaminopentane in some of the carbonate of the 1,5-diaminopentane, the 1,5-diaminopentane is not converted into a free form in the preparing of the basic composition. Thus, the separation of the 1,5-diaminopentane in a distillation step may be difficult. As a result, a recovery rate of the 1,5-diaminopentane may be reduced.

pH Adjustment Step (Basic Composition Preparation Step)

Next, a basic composition is prepared by adding a base to the carbonate removed acidic composition.

A pH may be adjusted by adding at least one base selected from the group consisting of sodium hydroxide, calcium hydroxide, magnesium hydroxide, potassium hydroxide, barium hydroxide, and ammonium hydroxide to the carbonate removed fermentation broth, i.e., the carbonate removed acidic composition. For example, the pH may be adjusted by adding sodium hydroxide. The pH of the basic composition may be adjusted to about 12.0 or more and, for example, may be adjusted to a range of about 12.0 to about 14.0. In a case where the pH of the basic composition is less than about 12.0, since a portion of the 1,5-diaminopentane may be present in a state of being combined with a salt, a subsequent separation of the 1,5-diaminopentane may be difficult. However, in a case where the pH of the basic composition is about 12.0 or more, since the salt combined with the 1,5-diaminopentane in the basic composition is separated, the distillation of the 1,5-diaminopentane may be facilitated. As a result, the recovery rate of the 1,5-diaminopentane may be improved.

Recovery Step

Figure 2:
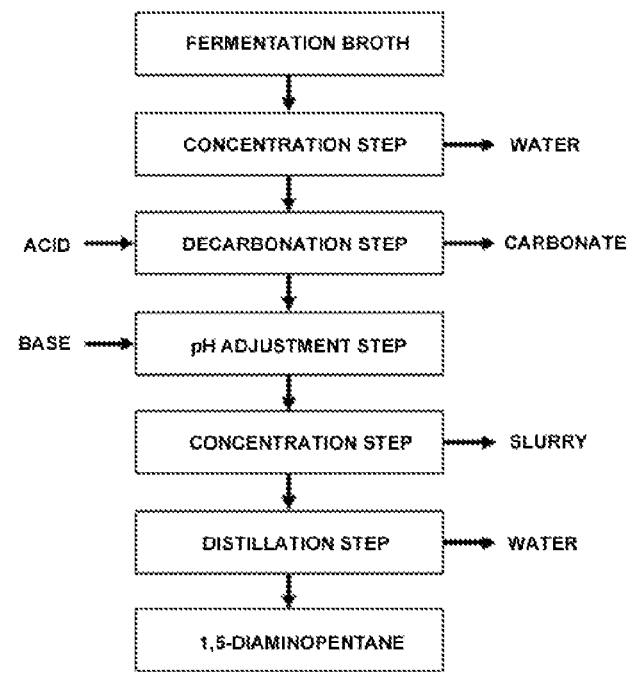
FIG. 2 is a flowchart specifically illustrating a recovery step in the refining method of Example 1.

The recovery step may be specifically divided into a secondary concentration step (or distillation step) and a fractional distillation step. However, the recovery step may actually be continuously performed. For example, the recovery step may be referred to FIGS. 1 and 2.

Secondary Concentration Step (Separation of Vapor and/or Condensate Including 1,5-Diaminopentane)

Next, a vapor and/or a condensate including 1,5-diaminopentane as a main component are recovered from the basic composition by distillation.

The basic composition is again introduced into the concentrator, and the secondary concentration step, for example, may be performed in a vacuum of about 10 to 760 mmHg or about 60 to 200 mmHg. The secondary concentration step, for example, may be performed in a temperature range of about 30 to 180° C. or about 40 to 120° C.

The evaporated vapor may be condensed and may then be introduced as a liquid into a distillation column, or may be directly introduced into the distillation column without the condensation. That is, the evaporated vapor may be used in the subsequent fractional distillation step.

Since a pH of a bottom liquid remaining in the concentrator is decreased as the 1,5-diaminopentane evaporates from the concentrator in the secondary concentration step, the pH of the bottom liquid may be maintained in a range of about 12.0 to about 14.0 by further adding a base. Also, in order to maintain the bottom liquid in a slurry state, a ratio of solid/liquid included in the slurry may be maintained in a range of about 0.1 to about 2.0, for example, about 0.5 to about 1.5, by constantly adding distilled water.

The slurry remaining in the secondary concentration step may be utilized as a by-product through an additional refining process. With respect to the fermentation broth from which the microorganism is not separated, the microorganism may be separated by further adding distilled water to completely dissolve the slurry, and a by-product may then be recovered from a mother liquor.

Fractional Distillation Step (Recovery of High-Purity 1,5-Diaminopentane)

High-purity 1,5-diaminopentane is separated from the vapor and/or the condensate including 1,5-diaminopentane as a main component which is generated in the secondary concentration step.

The secondary concentration step and the distillation step may be continuously performed. For example, the vapor including 1,5-diaminopentane, which is concentrated in the secondary concentration step, may be directly introduced into an intermediate height position of the distillation column for the fractional distillation step.

The fractional distillation step, for example, may be performed in a vacuum of about 10 to 760 mmHg or may be performed in a vacuum of about 60 to 200 mmHg. The fractional distillation step, for example, may be performed in a temperature range of about 30 to 180° C. or about 40 to 120° C.

Since the fractional distillation is conducted under the above-described pressure and temperature conditions, water and ammonia are separated from the top of the distillation column and 1,5-diaminopentane is separated from the bottom thereof.

The 1,5-diaminopentane refined by the above method may have a recovery rate of about 40 wt % or more, about 60 wt % or more, preferably about 65 wt % or more, more preferably about 75 wt % or more, even more preferably about 85 wt % or more, and most preferably 90.0 wt % or more.

Also, the 1,5-diaminopentane refined by the above method may have a purity of about 99.0 wt % or more and a recovery rate of about 90.0 wt % or more. The purity denotes purity with respect to components excluding a solvent. For example, the solvent may be water.

MODE OF THE INVENTIVE CONCEPT

Hereinafter, the inventive concept will be described in more detail, according to examples and comparative examples. However, the following examples are merely presented to exemplify the inventive concept, and the scope of the inventive concept is not limited thereto.

Refinement of 1,5-Diaminopentane

Example 1: Method of Refining 1,5-Diaminopentane

Fermentation Step

A fermentation broth including L-Lysine and its sulfate was prepared by culturing a microorganism, and, after removing the microorganism from the fermentation broth, a carboxylic group of L-Lysine may be removed by enzyme conversion reaction and thus, a fermentation broth including 1,5-diaminopentane may be prepared. In the prepared fermentation broth, an amount of the 1,5-diaminopentane in the form of carbonate was about 58% and an amount of the 1,5-diaminopentane in the form of sulfate was about 42%.

(Primary Concentration Step)

About 1,000 g of the 1,5-diaminopentane fermentation broth was introduced into a 1 L concentrator (Eyela) and was concentrated by removing about 60% of the fermentation broth while maintaining at a vapor temperature of about 47° C. and a pressure of about 80 mmHg. In this case, the removed condensed water was about 600 g and 1,5-diaminopentane was not detected in the removed condensed water. The following Table 1 is a composition analysis table before and after the primary concentration step. 1,5-diaminopentane, amino acid, organic acid, and ions of the following Table 1 were analyzed by high-performance liquid chromatography (HPLC) and moisture analysis was performed using a Karl-fisher moisture analysis method.

TABLE 1

| Component | Fermentation broth (g) | Residual liquid after primary concentration (g) | Condensed water removed after primary concentration (g) |
| --- | --- | --- | --- |
| Water | 760.6 | 160.6 | 600.0 |
| 1,5-diaminopentane | 123.4 | 123.4 | 0.0 |
| Amino acid | 1.5 | 1.5 | 0.0 |
| Ions | 110.2 | 110.2 | 0.0 |
| Organic acid | 1.1 | 1.1 | 0.0 |
| Microorganism | 3.2 | 3.2 | 0.0 |
| Total | 1,000.0 | 400.0 | 600.0 |

(Decarbonation Step)

About 70.8 g of sulfuric acid (purity 98%) was added to about 400 g of the residual liquid after the primary concentration to remove about 31.1 g of carbonate. A pH of an acidic composition obtained was about 4.5.

(pH Adjustment Step)

The pH of the concentrate was adjusted to about 13.4 by adding about 290.4 g of caustic soda (50% sodium hydroxide) having an equivalent molar ratio of 1,5-diaminopentane/sodium hydroxide of about 3 to about 439.7 g of the carbonate removed concentrate.

The following Table 2 is a composition analysis table in the decarboxylation and pH adjustment steps. 1,5-diaminopentane, amino acid, organic acid, and ions of the following Table 2 were analyzed by HPLC and moisture analysis was performed using a Karl-fisher moisture analysis method.

TABLE 2

| Component | Residual liquid after primary concentration (g) | Concentrate after adding sulphuric acid (g) | Concentrate after adding caustic soda (g) |
|---|---|---|---|
| Water | 160.6 | 174.8 | 381.7 |
| 1,5-diaminopentane | 123.4 | 123.4 | 123.4 |
| Amino acid | 1.5 | 1.5 | 1.5 |
| Ions | 110.2 | 135.7 | 219.2 |
| Organic acid | 1.1 | 1.1 | 1.1 |
| Microorganism | 3.2 | 3.2 | 3.2 |
| Total | 400.0 | 439.7 | 730.1 |

(Recovery Step: Secondary Concentration Step)

The residual liquid, to which the caustic soda was added, was introduced into a 1 L double-jacketed reactor. The top of the double-jacketed reactor was connected to a portion of a $10^{th}$ stage from the bottom of a tray-type distillation column (Aceglass Inc.) with a total of 20 stages. The residual liquid was further concentrated using the double-jacketed reactor at a vapour temperature of about 50° C. to about 130° C. and a pressure of about 80 mmHg. The vapour temperature in the double-jacketed reactor was initially maintained at about 47° C. due to the evaporation of water and was then increased to about 113° C. while 1,5-diaminopentane was evaporated. A vapor including 1,5-diaminopentane as a main component was introduced into the 20-stage distillation column.

(Recovery Step: Fractional Distillation Step)

About 459 g of water and 1,5-diaminopentane was recovered from the top of the distillation column by introducing the vapor including 1,5-diaminopentane as a main component into the 20-stage distillation column, about 111.2 g of 1,5-diaminopentane (HPLC purity 99.91 wt %, excluding water) was recovered from the bottom of the distillation column, and the recovery rate of the 1,5-diaminopentane was about 90.11 wt %.

1,5-diaminopentane was fractionally distilled using the distillation column at a vapour temperature of about 50° C. to about 113° C. and a pressure of about 80 mmHg.

The following Table 3 is a composition analysis table in the pH adjustment and recovery steps. 1,5-diaminopentane, amino acid, organic acid, and ions of the following Table 3 were analyzed by HPLC and moisture analysis was performed using a Karl-fisher moisture analysis method.

The recovery rate of the 1,5-diaminopentane obtained from the bottom of the distillation column was about 90.2 wt %.

Example 2

Refinement of 1,5-diaminopentane was performed in the same manner as in Example 1 except that the pH of a concentrate was adjusted to about 13.3 by adding about 242.0 g of caustic soda (50% sodium hydroxide) having an equivalent molar ratio of 1,5-diaminopentane/sodium hydroxide of about 2.5 to about 439.7 g of the carbonate removed concentrate.

The recovery rate of the 1,5-diaminopentane obtained from the bottom of the distillation column was about 86.9 wt %.

Reference Example 3

Refinement of 1,5-diaminopentane was performed in the same manner as in Example 1 except that the pH of a concentrate was adjusted to about 11.5 by adding about 193.6 g of caustic soda (50% sodium hydroxide) having an equivalent molar ratio of 1,5-diaminopentane/sodium hydroxide of about 2 to about 439.7 g of the carbonate removed concentrate.

The recovery rate of the 1,5-diaminopentane obtained from the bottom of the distillation column was about 42.6 wt %.

Comparative Example 1

Refinement of 1,5-diaminopentane was performed in the same manner as in Example 1 except that the pH of a concentrate was adjusted to about 13.8 by adding about 290.4 g of caustic soda (50% sodium hydroxide) having an equivalent molar ratio of 1,5-diaminopentane/sodium hydroxide of about 3 in the pH adjustment step without the decarbonation step.

The recovery rate of the 1,5-diaminopentane obtained from the bottom of the distillation column was about 63.0 wt %.

Comparative Example 2

Refinement of 1,5-diaminopentane was performed in the same manner as in Example 1 except that the pH of a

TABLE 3

| Component | Concentrate after adding caustic soda (g) | Concentrate recovered from the bottom of the distillation column (g) | Concentrate recovered from the top of the distillation column (g) | Reactor residual liquid (g) |
|---|---|---|---|---|
| Water | 381.7 | 0.1 | 357.9 | 23.7 |
| 1,5-diaminopentane | 123.4 | 111.2 | 1.1 | 11.1 |
| Amino acid | 1.5 | 0.0 | 0.0 | 1.5 |
| Ions | 219.2 | 0.0 | 0.0 | 219.2 |
| Organic acid | 1.1 | 0.0 | 0.0 | 1.1 |
| Microorganism | 3.2 | 0.0 | 0.0 | 3.2 |
| Total | 730.1 | 111.3 | 359.0 | 259.8 | concentrate was adjusted to about 13.5 by adding about 242.0 g of caustic soda (50% sodium hydroxide) having an equivalent molar ratio of 1,5-diaminopentane/sodium hydroxide of about 2.5 in the pH adjustment step without the decarbonation step.

The recovery rate of the 1,5-diaminopentane obtained from the bottom of the distillation column was about 61.2 wt %.

Comparative Example 3

Refinement of 1,5-diaminopentane was performed in the same manner as in Example 1 except that the pH of a concentrate was adjusted to about 13.5 by adding about 193.6 g of caustic soda (50% sodium hydroxide) having an equivalent molar ratio of 1,5-diaminopentane/sodium hydroxide of about 2.0 in the pH adjustment step without the decarbonation step.

The recovery rate of the 1,5-diaminopentane obtained from the bottom of the distillation column was about 30.0 wt %.

Evaluation Example 1

The recovery rates of the 1,5-diaminopentanes obtained in Examples 1 to 3 and Comparative Examples 1 to 3, the occurrence of the decarbonation of the primary concentrate, and the molar ratios of 1,5-diaminopentane/sodium hydroxide are listed in the following Table 4 to evaluate a difference in the recovery rate of 1,5-diaminopentane according to whether the decarboxylation of the primary concentrate occurred or not and changes in molar ratio of 1,5-diaminopentane/sodium hydroxide.

TABLE 4

| | Occurrence of Decarbonation | Molar ratio of 1,5-diaminopentane/ sodium hydroxide | pH of basic composition | Recovery rate of 1,5-diaminopentane [wt %] |
|---|---|---|---|---|
| Example 1 | ◯ | 3.0 | 13.4 | 90.2% |
| Example 2 | ◯ | 2.5 | 13.3 | 86.9% |
| Reference Example 3 | ◯ | 2.0 | 11.5 | 42.6% |
| Comparative Example 1 | X | 3.0 | 13.8 | 63.0% |
| Comparative Example 2 | X | 2.5 | 13.5 | 61.2% |
| Comparative Example 3 | X | 2.0 | 13.5 | 30.0% |

As illustrated in Table 4, the recovery rate of the 1,5-diaminopentane was significantly increased by adding the decarbonation step.

While the inventive concept has been particularly shown and described with reference to exemplary embodiments thereof, it will be understood that various changes in form and details may be made therein without departing from the spirit and scope of the following claims.

INDUSTRIAL APPLICABILITY

According to an aspect of the inventive concept, high-purity 1,5-diaminopentane may be obtained with a high yield by adding an acid to a fermentation broth including a carbonate of 1,5-diaminopentane in order to remove carbonate and then adding a base thereto.

The invention claimed is:

1. A method of refining 1,5-diaminopentane, the method comprising:
   fermenting a broth comprising L-Lysine and its sulfate to permit removal of a carboxyl group therefrom to prepare a carbonate and a sulfate of 1,5-diaminopentane, without adding an acid;
   concentrating a fermentation broth including the carbonate and the sulfate of 1,5-diaminopentane;
   adding an acid to the concentrated fermentation broth to prepare a carbonate removed acidic composition with a pH of about 4.0 to about 7.0;
   adding a base to the acidic composition to prepare a basic composition with a pH of about 12.0 to about 14; and
   recovering 1,5-diaminopentane from the basic composition.

2. The method of claim 1, wherein the concentrating of the fermentation broth is performed in a vapor temperature range of about 10° C. to about 100° C.

3. The method of claim 1, wherein the pH of the acidic composition is in a range of about 4.0 to about 5.0.

4. The method of claim 1, wherein the acid is at least one selected from the group consisting of hydrochloric acid, sulfuric acid, phosphoric acid, acetic acid, and nitric acid.

5. The method of claim 1, wherein the base is at least one selected from the group consisting of sodium hydroxide, calcium hydroxide, magnesium hydroxide, potassium hydroxide, barium hydroxide, and ammonium hydroxide.

6. The method of claim 1, wherein the recovering of the 1,5-diaminopentane from the basic composition comprises:
   separating a composition including 1,5-diaminopentane from the basic composition by distillation; and
   recovering 1,5-diaminopentane from the composition including 1,5-diaminopentane by fractional distillation.

7. The method of claim 6, wherein the separating of the composition including 1,5-diaminopentane as a main component by the distillation and the recovering of the 1,5-diaminopentane by the fractional distillation are continuously performed.

8. The method of claim 7, wherein the fractional distillation is performed in a distillation column and 1,5-diaminopentane is recovered from a bottom of the distillation column.

9. The method of claim 6, wherein a by-product is recovered from the basic composition from which the composition including 1,5-diaminopentane is removed.

* * * * *